United States Patent
Hoshino et al.

(12)

(10) Patent No.: US 6,190,695 B1
(45) Date of Patent: Feb. 20, 2001

(54) PHARMACEUTICAL COMPOSITION CONTAINING OSTEOGENESIS-PROMOTING SUBSTANCE

(75) Inventors: Tetsuo Hoshino, Toyono-gun; Kazuhiro Saito, Amagasaki; Susumu Iwasa, Kyotanabe, all of (JP)

(73) Assignee: Takeda Chemical Industries, Ltd., Osaka (JP)

( * ) Notice: Under 35 U.S.C. 154(b), the term of this patent shall be extended for 0 days.

(21) Appl. No.: 09/246,851

(22) Filed: Feb. 9, 1999

Related U.S. Application Data

(63) Continuation of application No. PCT/JP97/02941, filed on Aug. 25, 1997.

(30) Foreign Application Priority Data

Apr. 9, 1919 (JP) .................................................. 9-090408
Aug. 26, 1996 (JP) .................................................. 8-223443

(51) Int. Cl.⁷ .......................... A61K 9/20; A61K 31/445; A61K 31/66; A61K 31/40
(52) U.S. Cl. .......................... 424/464; 424/465; 514/108; 514/324; 514/428; 514/443; 514/448; 514/319
(58) Field of Search ..................... 514/108, 324, 514/428, 443, 319; 424/464, 465

(56) References Cited

FOREIGN PATENT DOCUMENTS

| | | |
|---|---|---|
| 0 328 806 | 8/1989 | (EP) . |
| 0 376 197 | 7/1990 | (EP) . |
| 0 460 488 A1 | 12/1991 | (EP) . |
| 0 719 782 A1 | 7/1996 | (EP) . |
| 6-321790 | 11/1994 | (JP) . |
| WO 94/23740 | 10/1994 | (WO) . |
| WO 96/39134 | 12/1996 | (WO) . |

OTHER PUBLICATIONS

Shimpei Miyamoto, M.D., Ph. D., et al. *Polylactic Acid–Polyethylene Glycol Block Copolymer*, Clinical Orthopaedics and Re;ated Research, No. 294, pp. 333–343, 1993.

Herbert P. Fiedler, *Lexikon der Hilfsstoffe für Pharmazie*, 1996, pp. 1210–1217.

Pai–chang Sheen, et al. International Journal of Pharmaceutics, vol. 118, pp. 221–227, 1995.

G.V. Betageri, et al. International Journal of Pharmaceutics, vol. 126, pp. 156–160, 1995.

*Primary Examiner*—T. J. Criares
(74) *Attorney, Agent, or Firm*—Foley & Lardner

(57) ABSTRACT

This invention provides a pharmaceutical composition comprising a non-peptide osteogenesis-promoting substance and a polyethylene glycol or a derivative thereof, which can be advantageously used as a agent for preventing or treating various bone diseases (e.g., osteoporosis) in view of the high oral absorbability and stability of the active ingredient.

30 Claims, No Drawings

PHARMACEUTICAL COMPOSITION CONTAINING OSTEOGENESIS-PROMOTING SUBSTANCE

This application is a Continuation of PCT International Application No. PCT/JP97/02941 filed Aug. 25, 1997 designating the United States.

TECHNICAL FIELD

The present invention relates to a preventive (prophylactic) or treating (therapeutic) agent for bone diseases comprising a non-peptide osteogenesis-promoting substance and polyethylene glycol or a derivative thereof.

BACKGROUND ART

There are two types of bone diseases: non-metabolic bone diseases, such as bone fractures, bone/spinal deformation, osteosarcoma, myeloma, bone dysplasia and scoliosis, and metabolic bone diseases, such as osteoporosis, osteomalacia, rickets, fibrous osteitis, renal bone dystrophy and Paget's disease of bone. In recent years, metabolic bone disease has increasingly became a problem. For example, osteoporosis, a metabolic bone disease, is a systemic disease characterized by increased bone fragility and fracturability due to decreased bone mass and change in fine bone tissue structure, its major clinical symptoms including spinal kyphosis, and fractures of dorsolumbar bones, vertebral centra, femoral necks, lower end of radius, ribs, upper end of humerus, and others. In bone tissue, bone formation and destruction due to bone resorption occur constantly with a good balance; osteoblasts and osteoclasts play key roles in osteogenesis and bone resorption, respectively. Upon deterioration of the balance between bone formation and bone destruction due to bone resorption, a quantitative reduction in bone occurs. Traditionally, bone resorption suppressors such as estrogens, calcitonin and bisphosphonates have been mainly used to treat osteoporosis.

Japanese Patent Unexamined Publication No. 232880/1991 describes a compound represented by the formula:

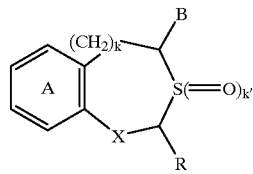

wherein ring A represents a benzene ring which may be substituted; R represents a hydrogen atom or a hydrocarbon group which may be substituted; B represents a carboxyl group which may be esterified or amidated; X represents —CH(OH)— or —CO—; k represents 0 or 1; and k' represents 0, 1 or 2; or a salt thereof, which is useful as a drug for treating osteoporosis.

Japanese Patent Unexamined Publication No. 364179/1992 describes a compound represented by the formula:

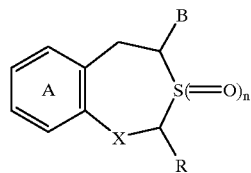

wherein ring A represents an optionally substituted benzene ring; R represents a hydrogen atom or an optionally substituted hydrocarbon group; B represents a carboxyl group which may be esterified or amidated; X represents CH(OH)— or —CO—; and n represents 0, 1 or 2; or a salt thereof, which is useful as a drug for treating osteoporosis.

EP-719782 describes an optically active compound represented by the formula:

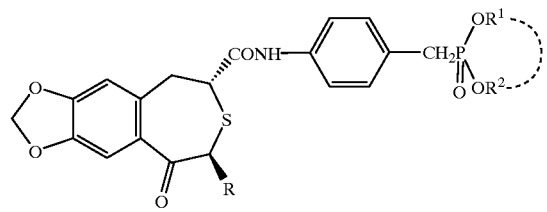

wherein R represents a lower alkyl group; $R_1$ and $R_2$ each represent a lower alkyl group, or may bind together to form a lower alkylene group, which compound is useful as a drug for treating osteoporosis.

On the other hand, the International Journal of Pharmaceutics, 118 (1995), pp. 221–227 describes a pharmaceutical preparation comprising a leukotriene B4 antagonist of the formula:

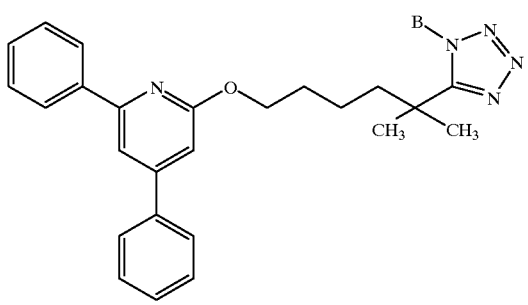

and polyethylene glycol 3350.

In the International Journal of Pharmaceutics, 126 (1995), pp. 155–160, a preparation for hypoglycemic agent comprising Glybride and polyethylene glycol 4000 or 6000 is described.

In the Clinical Orthopedics and Related Research, 294 p. 333 (1993), an implant comprising bone morphogenic protein (BMP) and polyethylene glycol 200 or 600 or a block polymer of polyethylene glycol and lactic acid is described.

Currently available pharmaceuticals used clinically to treat bone diseases fail to have a satisfactory effect in clinical situations, due to limitation on the subject of administration associated with the mechanism of action, or to problems in terms of side-effects and efficacy. Also, long and continuous administration is necessary in the prevention and treatment of osteoporosis; there is therefore a need for an easily administered oral preparation. However, some osteogenesis-promoting substances need to be improved as to bioavailability, stability and other aspects when administered as oral preparations. Therefore, a therapeutic drug for bone diseases that permit practical clinical use and that is effective not only in non-oral administration but also in oral administration is desired.

DISCLOSURE OF INVENTION

After extensive investigation aiming at resolving the above problems, the present inventors found that a pharmaceutical composition of a non-peptide osteogenesis-promoting substance containing polyethylene glycol or a derivative thereof has higher bioavailability than does one not containing polyethylene glycol, and that it surpasses conventional osteogenesis-promoting pharmaceutical compositions in terms of pharmaceutical properties, such as greater stability in blood. The present inventors made further investigation based on these findings, and developed the present invention. Accordingly, the present invention relates to:

(1) a pharmaceutical composition which comprises a non-peptide osteogenesis-promoting substance and a polyethylene glycol or a derivative thereof, (2) the pharmaceutical composition according to term (1), which is used for oral administration, (3) the pharmaceutical composition according to term (1), which is used for preventing or treating a bone disease, (4) the pharmaceutical composition according to term (3), wherein the bone disease is osteoporosis, (5) the pharmaceutical composition according to term (1), wherein the non-peptide osteogenesis-promoting substance is a compound represented by the formula or salt thereof:

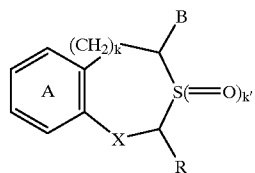

wherein ring A is an optionally substituted benzene ring; R is a hydrogen atom or an optionally substituted hydrocarbon group; B is an optionally esterified or amidated carboxyl group; X is —CH(OH)— or —CO—; k is 0 or 1; and k' is 0, 1 or 2, (6) the pharmaceutical composition according to term (5), wherein the ring A is a benzene ring which may be substituted by 1 or 2 substituents selected from the group consisting of halogen atoms, $C_{1-10}$ alkyl groups, $C_{1-10}$ alkoxy groups, alkylendioxy groups represented by the formula: —O—(CH$_2$)$_n$—O—, wherein n is an integer from 1 to 3 and $C_{1-10}$ alkylthio groups, (7) the pharmaceutical composition according to term (5), wherein B is an optionally substituted carbamoyl group of the formula: —CON(R$_1$)(R$_2$) wherein R$_1$ and R$_2$ are independently a hydrogen atom, an optionally substituted hydrocarbon group or an optionally substituted 5 to 7 membered heterocyclic group, (8) the pharmaceutical composition according to term (5), wherein R$_1$ is a hydrogen atom or a $C_{1-10}$ alkyl group, and R$_2$ is (i) a phenyl or phenyl-$C_{1-3}$ alkyl group which may be substituted by a halogen atom, a $C_{1-6}$ alkoxy group, a mono- or di-$C_{1-6}$ alkoxyphosphoryl group, a mono- or di-$C_{1-6}$ alkoxyphosphoryl-$C_{1-3}$ alkyl, a moiety of the formula:

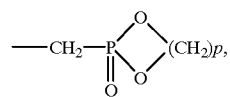

wherein p is an integer from 2 to 4, or a $C_{1-6}$ alkoxycarbonyl group or (ii) a 5- or 6-membered heterocyclic group containing 1 or 2 nitrogen atom(s) or 1 nitrogen atom and 1 sulfur atom, which may be substituted by a phenyl group, (9) the pharmaceutical composition according to term (5), wherein R is a hydrogen atom, a $C_{1-6}$ alkyl group or a phenyl group,

(10) the pharmaceutical composition according to term (5), wherein k is 1 and k' is 0,

(11) the pharmaceutical composition according to term (1), wherein the non-peptide osteogenesis-promoting substance is an optically active compound represented by the formula:

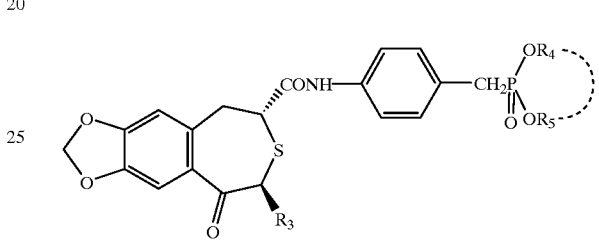

wherein R$_3$ is a lower alkyl group; and R$_4$ and R$_5$ are independently a lower alkyl group or bind together to form a lower alkylene group,

(12) the pharmaceutical composition according to term (11), wherein R$_3$, R$_4$ and R$_5$ are independently a $C_{1-6}$ alkyl group,

(13) the pharmaceutical composition according to term (1), wherein the non-peptide osteogenesis-promoting substance is (2R,4S)-(−)-N-[4-(diethoxyphosphorylmethyl) phenyl]-1,2,4,5-tetrahydro-4-methyl-7,8-methylenedioxy-5-oxo-3-benzothiepine-2-carboxamide,

(14) the pharmaceutical composition according to term (1), wherein the weight ratio of the polyethylene glycol or a derivative thereof relative to the non-peptide osteogenesis-promoting substance is from about 0.5 to about 2,000 times,

(15) the pharmaceutical composition according to term (14), which comprises (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide and a polyethylene glycol,

(16) the pharmaceutical composition according to term (15), wherein the weight ratio of (2R,4S)-(−)-N-[4-diethoxyphosphorylmethyl)phenyl]-1,2,4,5-tetrahydro-4-methyl-7,8-methylenedioxy-5-oxo-3-benzothiepine-2-carboxamide relative to the pharmaceutical composition is about 0.05 to about 70% (w/w),

(17) the pharmaceutical composition according to term (1), wherein the weight-average molecular weight of the polyethylene glycol is about 200 to about 9,000,

(18) the pharmaceutical composition according to term (1), wherein the derivative of polyethylene glycol is a polyglycolized glyceride,

(19) the pharmaceutical composition according to term (18), wherein the HLB of the polyglycolized glyceride is not less than 8,

(20) a pharmaceutical composition according to term (1), which further comprises a glycerin fatty acid ester,

(21) the pharmaceutical composition according to term (20), wherein the glycerin fatty acid ester is a fatty acid triglyceride,

(22) a pharmaceutical composition which is produced by removing the organic solvent from a solution comprising a non-peptide osteogenesis-promoting substance and a polyethylene glycol or derivative thereof in an organic solvent,

(23) a method for producing the pharmaceutical composition of term (1), which comprises dissolving a non-peptide osteogenesis-promoting substance and a polyethylene glycol or derivative thereof in an organic solvent, and removing the solvent,

(24) the method according to term (23), wherein the organic solvent comprises 1 to 3 solvent(s) selected form the group consisting of alcohols, acetonitrile, aromatic hydrocarbons, halogenated hydrocarbons and fatty acid esters,

(25) the method according to term (23), wherein the solvent further comprises propylene glycol,

(26) the method according to term (23), wherein the solvent is methanol, ethanol or acetonitrile,

(27) the method according to term (23), wherein the concentration in the organic solvent solution of the non-peptide osteogenetic promoting substance is from about 0.01% (w/w) to about 80% (w/w),

(28) a method for treating or preventing bone diseases in mammals which comprises administrating to a subject in need an effective amount of a pharmaceutical composition according to term (1), and

(29) use of the pharmaceutical composition according to term (1) for manufacturing a medicament for treating or preventing bone diseases.

The non-peptide osteogenesis-promoting substance used in the present invention is exemplified by the sulfur-containing heterocyclic compounds described in Japanese Patent Unexamined Publication Nos. 232880/1991, 364179/1992 and 294960/1993 (e.g., (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide) or salts thereof, the benzopyrane derivatives described in Japanese Patent Unexamined Publication No. 291983/1995 (e.g., N-(4-diethoxyphosphorylmethylphenyl)-4-oxo-4H-1-benzopyrane-2-carboxamide) or salts thereof, the phosphonic acid derivatives described in WO96/01267 (e.g., diethyl 4-(7-cyclohexyl-3,4-dihydro-2-naphthalenecarboxamide) benzylphosphonate)) or salts thereof, the prostaglandin $A_1$ derivatives described in the Journal of Pharmacology and Experimental Therapeutics, vol. 258, pp. 1,120–1,126 (1991), the vitamin $D_3$ derivatives described in Bioorganic & Medicinal Chemistry Letters, vol. 3, pp. 1,815–1,819 (1993), the benzylphosphonic acid derivatives described in EP-524023, the bisphosphonic acids described in Bone, vol. 13, pp. 249–255 (1992), and the vitamin $K_2$ derivatives described in Biochemical and Biophysical Research Communications, vol. 187, pp. 814–820 (1992); of these non-peptide osteogenesis-promoting substances, non-steroidal compounds are commonly used. These may be used in combination of two or more kinds at appropriate ratios.

Of the above-mentioned non-peptide osteogenesis-promoting substances, the compounds represented by formula (I):

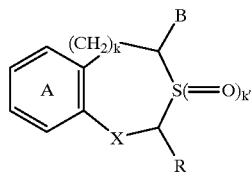

wherein ring A is an optionally substituted benzene ring; R is a hydrogen atom or an optionally substituted hydrocarbon group; B is an optionally esterified or amidated carboxyl group; X is —CH(OH)— or —CO—; k represents 0 or 1; k' is 0, 1 or 2; or a salt thereof, for example, are preferably used.

With respect to the formula (I), the substituent(s) for the substituted benzene ring represented by ring A are exemplified by halogen atoms, nitro groups, optionally substituted alkyl groups, optionally substituted hydroxyl groups, optionally substituted thiol groups, optionally substituted amino groups, optionally substituted acyl groups, mono- or di-alkoxyphosphoryl groups, phosphono groups, optionally substituted aryl groups, optionally substituted aralkyl groups, and optionally substituted aromatic heterocyclic groups. Of these substituents, 1 to 4, preferably 1 to 2, whether identical or not, may be present on the benzene ring.

The halogen atoms include, for example, fluorine, chlorine, bromine and iodine.

The alkyl groups of the optionally substituted alkyl groups are preferably alkyl groups having 1 to 10 carbon atoms (e.g., methyl, ethyl, propyl, isopropyl, butyl, isobutyl, sec-butyl, tert-butyl, pentyl, isopentyl, neopentyl, hexyl, heptyl, octyl, nonyl, decyl) and cycloalkyl groups having 3 to 7 carbon atoms (e.g., cyclopropyl, cyclobutyl, cyclohexyl, cycloheptyl). These alkyl groups may be substituted for by 1 to 3 substituents selected from halogens (e.g., fluorine, chlorine, bromine, iodine), hydroxyl groups, alkoxy groups having 1 to 6 carbon atoms (e.g., methoxy, ethoxy, propoxy, butoxy, hexyloxy), mono- or di-($C_{1-6}$ alkoxy)phosphoryl groups (e.g., methoxyphosphoryl, ethoxyphosphoryl, dimethoxyphosphoryl, diethoxyphosphoryl), phosphono groups, etc.

Substituted alkyl groups include, for example, trifluoromethyl, trifluoroethyl, trichloromethyl, hydroxymethyl, 2-hydroxyethyl, methoxyethyl, 1-methoxyethyl, 2-methoxyethyl, 2,2-diethoxyethyl, 2-diethoxyphosphorylethyl, phosphono groups and phosphonomethyl groups.

The hydroxyl groups of the optionally substituted hydroxyl groups include, for example, alkoxy groups, alkenyloxy groups, aralkyloxy groups, acyloxy groups and aryloxy groups. The alkoxy groups are preferably alkoxy groups having 1 to 10 carbon atoms (e.g., methoxy, ethoxy, propoxy, butoxy, tert-butoxy, pentyloxy, hexyloxy, heptyloxy, nonyloxy) and cycloalkoxy groups having 4 to 6 carbon atoms (e.g., cyclobutoxy, cyclopentoxy, cyclohexyloxy). The alkenyloxy groups are preferably alkenyloxy groups having 2 to 10 carbon atoms, e.g., allyloxy, crotyloxy, 2-pentenyloxy, 3-hexenyloxy, 2-cyclopentenylmethoxy and 2-cyclohexenylmethoxy. The aralkyloxy groups are preferably aralkyloxy groups having 6 to 19 carbon atoms, more preferably $C_{6-014}$ aryl-$C_{1-4}$ aralkyloxy groups (e.g., benzyloxy, phenethyloxy). The acyloxy groups are preferably alkanoyloxy groups, e.g., alkanyloxy groups having 2 to 10 carbon atoms (e.g., acetyloxy, propionyloxy, n-butyryloxy, hexanoyloxy). The aryloxy groups are preferably aryloxy groups having 6 to 14 carbon atoms (e.g., phenoxy, biphenyloxy). These groups may be further substituted for by 1 to 3 substituents, e.g., the above-mentioned halogen atoms, hydroxyl groups, alkoxy groups having 1 to 6 carbon atoms, mono- or di-($C_{1-6}$ alkoxy)phosphoryl groups. Substituted hydroxyl groups include, for example, trifluoromethoxy, 2,2,2-trifluoroethoxy, difluoromethoxy, 2-methoxyethoxy, 4-chlorobenzyloxy and 2-(3,4-dimethoxyphenyl)ethoxy.

The thiol groups of the optionally substituted thiol groups include, for example, alkylthio groups, aralkylthio groups and acylthio groups. The "alkylthio groups" are preferably alkylthio groups having 1 to 10 carbon atoms (e.g., methylthio, ethylthio, propylthio, butylthio, pentylthio, hexylthio, heptylthio, nonylthio) and cycloalkylthio groups having 4 to 6 carbon atoms (e.g., cyclobutylthio, cyclopentylthio, cyclohexylthio). The aralkylthio groups are preferably aralkylthio groups having 7 to 19 carbon atoms, more preferably $C_{6-14}$ aryl-$C_{1-4}$ alkylthio groups, e.g., benzylthio, phenethylthio. The acylthio groups are preferably alkanoylthio groups, e.g., alkanoylthio groups having 2 to 10 carbon atoms (e.g., acetylthio, propionylthio, n-butyrylthio, hexanoylthio). These groups may be further substituted for by 1 to 3 substituents, e.g., the above-mentioned halogen atoms, hydroxyl groups, alkoxy groups having 1 to 6 carbon atoms, mono- or di-($C_{1-6}$ alkoxy) phosphoryl groups. The specific example of the substituted thiol groups include groups such as trifluoromethylthio, 2,2,2-trifluoroethylthio, 2-methoxyethylthio, 4-chlorobenzylthio, 3,4-dichlorobenzylthio, 4-fluorobenzylthio and 2-(3,4-dimethoxyphenyl)ethylthio.

As substituents for the substituted amino group of the optionally substituted amino groups there may be used 1 or 2 identical or different substituents selected from the above-mentioned alkyl groups having 1 to 10 carbon atoms, alkenyl groups having 2 to 10 carbon atoms (e.g., allyl, vinyl, 2-penten-1-yl, 3-penten-1-yl, 2-hexen-1-yl, 3-hexen-1-yl, 2-cyclohexenyl, 2-cyclopentenyl, 2-methyl-2-propen-1-yl, 3-methyl-2-buten-1-yl), alkyl groups having 6 to 14 carbon atoms, and aralkyl groups having 7 to 19 carbon atoms. These groups may be substituted for by the above-mentioned halogen atoms, alkoxy groups having 1 to 6 carbon atoms, mono- or di-($C_{1-6}$ alkoxy)phosphoryl groups, phosphono groups, etc. The specific examples of the substituted amino groups include groups such as methylamino, dimethylamino, ethylamino, diethylamino, dibutylamino, diallylamino, cyclohexylamino, phenylamino, N-methyl-N-phenylamino, N-methyl-N-(4-cyclobenzyl)amino, and N,N-di(2-methoxyethyl)amino.

The acyl groups include organic carboxylic acyl groups and sulfonic acyl groups having hydrocarbon groups having 1 to 6 carbon atoms (e.g., methyl, ethyl, n-propyl, hexyl, phenyl). The organic carboxylic acyl groups include, for example, formyls, $C_{1-10}$ alkyl-carbonyl groups (e.g., acetyl, propionyl, butyryl, valeryl, pivaloyl, hexanoyl, octanoyl, cyclobutanecarbonyl, cyclohexanecarbonyl, cycloheptanecarbonyl), $C_{2-10}$ alkenyl-carbonyl groups (e.g., crotonyl, 2-cyclohexenecarbonyl), $C_{6-14}$ aryl-carbonyl groups (e.g., benzoyl), $C_{7-19}$ aralkyl-carbonyl groups (e.g., benzylcarbonyl, benzhydrylcarbonyl), 5- or 6-membered aromatic heterocyclic carbonyl groups (e.g., nicotinoyl, 4-thiazolylcarbonyl), 5- or 6-membered aromatic heterocyclic acetyl groups (e.g., 3-pyridylacetyl, 4-thiazolylacetyl). The "sulfonic acyl groups having hydrocarbon groups having 1 to 6 carbon atoms" include, for example, methanesulfonyl and ethanesulfonyl. These groups may be further substituted for by 1 to 3 substituents, e.g., the above-mentioned halogen atoms, hydroxyl groups, alkoxy groups having 1 to 6 carbon atoms, amino groups. Examples of acyl groups include, for example, trifluoroacetyl, trichloroacetyl, 4-methoxybutyryl, 3-cyclohexyloxypropionyl, 4-chlorobenzoyl and 3,4-dimethoxybenzoyl.

The mono- or di-alkoxyphosphoryl groups include, for example, mono-$C_{1-6}$ alkoxyphosphoryl groups such as methoxyphosphoryl, ethoxyphosphoryl, propoxyphosphoryl, isopropoxyphosphoryl, butoxyphosphoryl, pentyloxyphosphoryl and hexyloxyphosphoryl, and di-$C_{1-6}$ alkoxyphosphoryl groups such as dimethoxyphosphoryl, diethoxyphosphoryl, dipropoxyphosphoryl, diisopropoxyphosphoryl, dibutoxyphosphoryl, dipentyloxyphosphoryl and dihexyloxyphosphoryl, with preference given to di-$C_{1-6}$ alkoxyphosphoryl groups, e.g., dimethoxyphosphoryl, diethoxyphosphoryl, dipropoxyphosphoryl, diisopropoxyphosphoryl, ethylenedioxyphosphoryl and dibutoxyphosphoryl.

The aryl groups of the optionally substituted aryl groups are preferably aryl groups having 6 to 14 carbon atoms, e.g., phenyl, naphthyl and anthryl. These groups may be further substituted for by 1 to 3 substituents, e.g., the above-mentioned alkyl groups having 1 to 10 carbon atoms, halogen atoms, hydroxyl groups, alkoxy groups having 1 to 6 carbon atoms, etc. Examples of substituted aryl groups include, for example, 4-chlorophenyl, 3,4-dimethoxyphenyl, 4-cyclohexylphenyl and 5,6,7,8-tetrahydro-2-naphthyl.

The aralkyl groups of the optionally substituted aralkyl groups are preferably aralkyl groups having 7 to 19 carbon atoms, e.g., benzyl, naphthylethyl and trityl. These groups may be substituted for by 1 to 3 substituents, e.g., the above-mentioned alkyl groups having 1 to 10 carbon atoms, halogen atoms, hydroxyl groups, alkoxy groups having 1 to 6 carbon atoms, etc. on the aromatic ring. Examples of substituted aralkyl groups include, for example, 4-chlorobenzyl, 3,4-dimethoxybenzyl, 4-cyclohexylbenzyl and 5,6,7,8-tetrahydro-2-naphthylethyl.

The aromatic heterocyclic groups of the optionally substituted aromatic heterocyclic groups are preferably 5- to 6-membered aromatic heterocyclic groups having 1 to 4 nitrogen atoms, oxygen atoms and/or sulfur atoms, e.g., furyl, thienyl, imidazolyl, thiazolyl, oxazolyl and thiadiazolyl. These groups may be substituted for by 1 to 3 substituents, e.g., the above-mentioned alkyl groups having 1 to 10 carbon atoms, halogen atoms, hydroxyl groups, alkoxy groups having 1 to 6 carbon atoms, etc. Examples of substituted aryl groups include, for example, 4-chlorophenyl, 3,4-dimethoxyphenyl, 4-cyclohexylphenyl and 5,6,7,8-tetrahydro-2-naphthyl.

Provided that two alkyl groups are present as adjoining substituents on benzene ring A, they may bind together to form an alkylene group represented by the formula —$(CH_2)_m$—, wherein m represents an integer from 3 to 5 (e.g., trimethylene, tetramethylene, pentamethylene). Provided that two alkoxy groups are present as adjoining substituents, they may bind together to form an alkylenedioxy group represented by the formula: —O—$(CH_2)_n$—O—, wherein (n represents an integer from 1 to 3 (e.g., methylenedioxy, ethylenedioxy, trimethylenedioxy). In these cases, a 5- to 7-membered ring is formed together with the carbon atoms of the benzene ring.

With respect to formula (I) above, R represents a hydrogen atom or an optionally substituted hydrocarbon group.

The hydrocarbon group of the optionally substituted hydrocarbon group represented by R include, for example, the above-mentioned alkyl groups (preferably alkyl groups having 1 to 10 carbon atoms), alkenyl groups (preferably alkenyl groups having 2 to 10 carbon atoms), aryl groups (preferably aryl groups having 6 to 14 carbon atoms) and aralkyl groups (preferably aralkyls having 7 to 19 carbon atoms). As substituents on the hydrocarbon group, there may be used the above-mentioned 5- to 6-membered aromatic heterocyclic groups, halogen atoms, di-$C_{1-6}$ alkoxyphosphoryl groups and phosphono groups.

R is preferably an unsubstituted alkyl group having 1 to 6 carbon atoms, such as methyl, ethyl, propyl, isopropyl, butyl, isobutyl, sec-butyl, tert-butyl, pentyl, neopentyl and hexyl.

With respect to formula (I), B is an optionally substituted carboxyl group.

The esterified carboxyl groups of the optionally esterified carboxyl group represented by B include, for example, alkoxycarbonyl groups, preferably $C_{1-10}$ alkoxycarbonyl groups (e.g., methoxycarbonyl, ethoxycarbonyl, propoxycarbonyl, butoxycarbonyl), aryloxy-carbonyl groups, preferably aryloxy-carbonyl groups having 6 to 14 carbon atoms (e.g., phenoxycarbonyls), and aralkyloxycarbonyl groups, preferably aralkyloxy-carbonyl groups having 7 to 19 carbon atoms (e.g., benzyloxycarbonyl).

The amidated carboxyl group of the optionally amidated carboxyl group represented by B include, for example, a carbamoyl group represented by the formula: —CON($R_1$)($R_2$), wherein $R_1$ and $R_2$ each represent a hydrogen atom, an optionally substituted hydrocarbon group, or an optionally substituted 5- to 7-membered heterocyclic group.

The hydrocarbon group of the optionally substituted hydrocarbon group represented by $R_1$ or $R_2$ is exemplified by alkyl groups, preferably alkyl groups having 1 to 10 carbon atoms (e.g., methyl, ethyl, propyl, isopropyl, butyl, isobutyl, sec-butyl, tert-butyl, pentyl, isopentyl, neopentyl, hexyl, heptyl, octyl, nonyl, decyl), alkenyl groups, preferably alkenyl groups having 2 to 10 carbon atoms (e.g., allyl, vinyl, 2-penten-1-yl, 3-penten-1-yl, 2-hexen-1-yl, 3-hexen-1-yl, 2-cyclohexenyl, 2-cyclopentenyl, 2-methyl-2-propen-1-yl, 3-methyl-2-buten-1-yl), aryl groups, preferably aryl groups having 6 to 14 carbon atoms (e.g., phenyl, naphthyl, anthryl), and aralkyl groups, preferably aralkyl groups having 7 to 19 carbon atoms (e.g., benzyl, naphthylethyl, trityl). These hydrocarbon groups may be substituted for by 1 to 3 substituents selected from (i) halogen atoms (e.g., fluorine, chlorine, bromine, iodine), (ii) hydroxyl groups, (iii) alkoxy groups having 1 to 6 carbon atoms (e.g., methoxy, ethoxy, propoxy, butoxy, tert-butoxy, pentyloxy, hexyloxy), (iv) amino groups which may be substituted by alkyl groups having 1 to 6 carbon atoms (e.g., methyl, ethyl, propyl, isopropyl, butyl, isobutyl, sec-butyl, tert-butyl, pentyl, isopentyl, neopentyl, hexyl) (e.g., amino, methylamino, ethylamino, dimethylamino, diethylamino, dipropylamino), (v) amino groups substituted for by acyl groups (e.g. alkanoyl groups having 1 to 10 carbon atoms) (e.g., acetylamino, propionylamino, benzoylamino), (vi) carbamoyl groups that may be substituted for by alkyl groups having 1 to 6 carbon atoms (carbamoyl, methylcarbamoyl, dimethylcarbamoyl, diethylcarbamoyl), (vii) alkoxy-carbonyls having 1 to 6 carbon atoms (e.g., methoxycarbonyl, ethoxycarbonyl, propoxycarbonyl), (viii) mono- or di-alkoxyphosporyl groups [e.g., mono- or di-$C_{1-6}$ alkoxyphosphoryl groups (e.g., dimethoxyphosphoryl, diethoxyphosphoryl, ethylenedioxyphosphoryl)], (ix) mono- or di-alkoxyphosphorylalkyl groups [e.g., mono- or di-$C_{1-6}$ alkoxyphosphoryl-$C_{1-3}$ alkyl groups (e.g., methoxyphosphorylmethyl, ethoxyphosphorylmethyl, methoxyphosphorylethyl, ethoxyphosphorylethyl, dimethoxyphosphorylmethyl, diethoxyphosphorylmethyl, dimethoxyphosphorylethyl, diethoxyphosphorylethyl)], (x) groups represented by the formula:

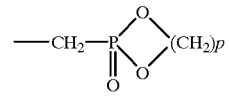

wherein p represents an integer from 2 to 4, (xi) phosphono groups, (xii) aromatic heterocyclic groups (having the same definition as that shown above), etc.

The 5- to 7-membered heterocyclic groups of the optionally substituted 5- to 7-membered heterocyclic groups represented by $R_1$ or $R_2$ include 5- to 7-membered heterocyclic groups containing 1 sulfur atom, nitrogen atom or oxygen atom, 5- to 6-membered heterocyclic groups containing 2 to 4 nitrogen atoms, and 5- to 6-membered heterocyclic groups containing 1 or 2 nitrogen atoms and 1 sulfur atom or oxygen atom. These heterocyclic groups may condense with a 6-membered ring containing 2 or fewer nitrogen atoms, a benzene ring, or a 5-membered ring containing 1 sulfur atom. As the substituents of the optionally substituted 5- to 7-membered heterocyclic group there may be used 1 to 4 of the same substituents as those for the optionally substituted hydrocarbon groups represented by $R_1$ or $R_2$ above.

Preferable examples of the 5- to 7-membered heterocyclic group represented by $R_1$ or $R_2$ include, for example, 2-pyridyl, pyrimidinyl, pyrazinyl, pyridazinyl, pyrazolyl, imidazolyl, thiazolyl, oxazolyl, pyrido[2,3-d]pyrimidyl, benzopyranyl, 1,8-naphthylidyl, quinolyl, thieno[2,3-b]pyridyl, tetrazolyl, thiadiazolyl, oxadiazolyl, triazinyl, triazolyl, thienyl, pyrrolyl, pyrrolinyl, furyl, pyrrolidinyl, benzothienyl, indolyl, imidazolidinyl, piperidyl, piperidino, piperazinyl, morpholinyl and morpholino.

$R_1$ and $R_2$ may bind together to form a 5- to 7-membered ring of the formula -N$R_1$($R_2$). Such rings include, for example, morpholine, piperidine, thiomorpholine, homopiperidine, piperidine, pyrrolidine, thiazolidine and azepine.

Examples of substituted alkyl groups as preferable examples of the "optionally substituted hydrocarbon group" represented by $R_1$ or $R_2$ include, for example, trifluoromethyl, trifluoroethyl, difluoromethyl, trichloromethyl, 2-hydroxyethyl, 2-methoxyethyl, 2-ethoxyethyl, 2,2-dimethoxyethyl, 2,2-diethoxyethyl, 2-pyridylmethyl, 2-(2-thienyl)ethyl, 3-(3-furyl)propyl, 2-morpholinoethyl, 3-pyrrolylbutyl, 2-piperidinoethyl, 2-(N,N-dimethylamino)ethyl, 2-(N-methyl-N-ethylamino)ethyl, 2-(N,N-dimethylamino)ethyl, 2-(N-methyl-N-ethylamino)ethyl, 2-(N,N-diisopropylamino)ethyl, 5-(N,N-dimethylamino)pentyl, N,N-dimethylcarbamoylethyl, N,N-dimethylcarbamoylpentyl, ethoxycarbonylmethyl, isopropoxycarbonylethyl, tert-butoxycarbonylpropyl, 2-diethoxyphosphorylethyl, 3-dipropoxyphosphorylpropyl, 4-dibutoxyphosphorylbutyl, ethylenedioxyphosphorylmethyl, 2-phosphonoethyl and 3-phosphonoethyl. The specific examples of substituted aralkyl groups include, for example, 4-chlorobenzyl, 3-(2-fluorophenyl)propyl, 3-methoxybenzyl, 3,4-dimethoxyphenethyl, 4-ethylbenzyl, 4-(3-trifluoromethylphenyl)butyl, 4-acetylaminobenzyl, 4-dimethylaminophenethyl, 4-diethoxyphosphorylbenzyl, and 2-(4-dipropoxyphosphorylmethylphenyl)ethyl. The specific examples of the substituted aryl groups include, 4-chlorophenyl, 4-cyclohexylphenyl, 5,6,7,8-tetrahydro-2-naphthyl, 3-triluofomethylphenyl, 4-hydroxyphenyl, 3,4,5-trimethoxyphenyl, 6-methoxy-2-naphthyl, 4-(4- chlorobenzyloxy)phenyl, 3,4-methylenedioxyphenyl, 4-(2,2,2-trifluoroethoxy)phenyl, 4-propionylphenyl, 4-cyclohexanecarbonylphenyl, 4-dimethylaminophenyl, 4-benzoylaminophenyl, 4-diethoxycarbamoylphenyl, 4-tert-butoxycarbonylphenyl, 4-diethoxyphosphorylphenyl, 4-diethoxyphosphorylmethylphenyl, 4-(2-diethoxyphosphorylethyl)phenyl, 2-diethoxyphosphorylmethylphenyl, 3-diethoxyphosphorylmethylphenyl, 4-dipropoxyphosphorylphenyl, 4-(2-phosphonoethyl)phenyl, 4-phosphonomethylphenyl and 4-phosphonophenyl. The specific examples of substituted 5- to 7-membered heterocyclic groups include, 5-chloro-2-pyridyl, 3-methoxy-2-pyridyl, 5-methyl-2-benzothiazolyl, 5-methyl-4-phenyl-2-thiazolyl, 3-phenyl-5-isoxazolyl, 4-(4-chlorophenyl)-5-methyl-2-oxazolyl, 3-phenyl-1,2,4-thiadiazol-5-yl, 5-methyl-1,3,4-thiadiazol-2-yl, 5-acetylamino-2-pyrimidyl, 3-methyl-2-thienyl, 4,5-dimethyl-2-furanyl and 4-methyl-2-morpholinyl.

With respect to the formula (I), ring A is preferably a benzene ring which may be substituted by 1 or more, more preferably 1 or 2, identical or different substituents selected from the above-mentioned halogen atoms, optionally substituted alkyl groups, optionally substituted hydroxyl groups, optionally substituted thiol groups and/or optionally substituted amino groups.

More preferably, ring A is a benzene ring which may be substituted for by 1 or 2 identical or different substituents selected from halogen atoms, alkyl groups having 1 to 10 (more preferably 1 to 5) carbon atoms, alkoxy groups having 1 to 10 (more preferably 1 to 5) carbon atoms, alkylenedioxy groups represented by the formula: —O—(CH$_2$)$_n$—O—, wherein n represents an integer from 1 to 3, and/or alkylthio groups having 1 to 10, more preferably 1 to 5, carbon atoms.

Particularly preferable examples of ring A are benzene rings substituted by an alkylenedioxy group represented by the formula: —O—(CH$_2$)$_n$—O—, wherein n represents an integer from 1 to 3.

B is preferably an alkoxy-heterocyclic group, a group represented by —CON(R$_1$)(R$_2$) (R$_1$ and R$_2$ each represent a hydrogen atom, an optionally substituted hydrocarbon group, or an optionally substituted 5- to 7-membered heterocyclic group).

With respect with preferable examples of R$_1$ and R$_2$, R$_1$ is a hydrogen atom and an alkyl group having 1 to 10 carbon atoms (e.g., methyl, ethyl, propyl) and R$_2$ is a phenyls or a phenyl-C$_{1-3}$ alkyl group that may be substituted for by halogens (e.g., fluorine, chlorine, bromine), C$_{1-6}$ alkoxys (e.g., methoxy, ethoxy), mono- or di-alkoxyphosphoryls (e.g., mono- or di-C$_{1-6}$ alkoxyphosphoryls such as dimethoxyphosphoryl and diethoxyphosphoryl), mono- or di-alkoxyphosphorylalkyls (e.g., mono- or di-C$_{1-6}$ alkoxyphosphoryl-C$_{1-3}$ alkyls such as dimethoxyphosphorylmethyl and diethoxyphosphorylmethyl) or C$_{1-6}$ alkoxycarbonyls (e.g., methoxycarbonyl, ethoxycarbonyl), and 5- or 6-membered heterocyclic groups that have 1 or 2 nitrogen atoms or 1 nitrogen atom and 1 sulfur atom, and that may be substituted by a phenyl group (e.g., pyridyl).

More preferably, R$_1$ is a hydrogen atom and R$_2$ is a phenyl group substituted by a mono- or di-C$_{1-6}$ alkoxyphosphoryl-C$_{1-3}$ alkyl (e.g., 4-diethoxyphosphorylmethylphenyl).

With respect to the formula (I), X is —CH(OH)— or CO—, preferably —CO—.

With respect to the formula (I), k is 0 or 1 and k' is 0, 1 or 2, preferably k is 1 and k' is 0.

R is preferably a hydrogen atom, a C$_{1-6}$ alkyl group (e.g., methyl, ethyl) or a phenyl group.

A more preferable example of compound (I) is an optically active benzothiepine derivative represented by formula (II):

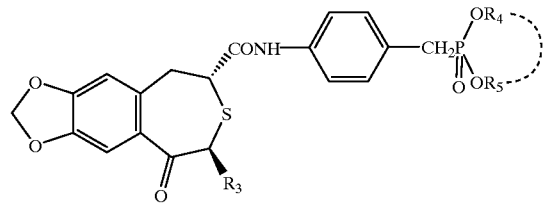

wherein R$_3$ is a lower alkyl group; R$_4$ and R$_5$ are independently a lower alkyl group, or may bind together to represent a lower alkylene group.

With respect to formula (II) above, the lower alkyl group represented by R$_3$, R$_4$ or R$_5$ is exemplified by alkyl groups having 1 to 6 (preferably 1 to 4) carbon atoms, such as methyl, ethyl, propyl, isopropyl, butyl, isobutyl, sec-butyl, tert-butyl, pentyl, isopentyl, neopentyl, hexyl). R$_4$ and R$_5$ may bind together to form a lower alkylene group. In this case, a moiety:

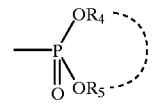

can be represented by a moiety:

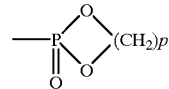

(in these formulas, p is an integer from 2 to 4).

R$_3$, R$_4$ and R$_5$ are each preferably an alkyl group having 1 to 4 carbon atoms, such as methyl or ethyl.

Compound (II) is preferably an optically active isomer of the (2R,4S) configuration containing substantially no compound of the (2S,4R) configuration, and having an optical purity of as close to 100% as possible.

Preferable examples of compound (II) include, for example, (2R,4S)-(-)-N-[4-(diethoxyphosphorylmethyl)phenyl]-1,2,4,5-tetrahydro-4-methyl-7,8-methylenedioxy-5-oxo-3-benzothiepine-2-carboxamide (hereinafter also referred to as compound A) or a salt thereof.

The salt of the non-peptide osteogenesis-promoting substance for the present invention is preferably a pharmacologically acceptable salt. Such pharmacologically acceptable salts include salts with inorganic bases, salts with organic bases, and salts with basic or acidic amino acids. Regarding inorganic bases capable of forming a salt of a non-peptide osteogenesis-promoting substance include alkali metals (e.g., sodium, potassium) and alkaline earth metals (e.g., calcium, magnesium); such organic bases include, for example, trimethylamine, triethylamine, pyridine, picoline, N,N'-dibenzylethylenediamine and diethanolamine; such inorganic acids include hydrochloric acid, hydrobromic acid, hydroiodic acid, phosphoric acid, nitric acid and sulfuric acid; such organic acids include formic acid, acetic acid, trifluoroacetic acid, oxalic acid, tartaric acid, fumaric acid, maleic acid, methanesulfonic acid, benzenesulfonic acid, p-toluenesulfonic acid and citric acid; such basic or acidic amino acids include, for example, arginine, lysine, aspartic acid and glutamic acid.

Of the non-peptide osteogenesis-promoting substances used in the present invention, sulfur-containing heterocyclic compounds, for example, are produced by the methods described in Japanese Patent Unexamined Publication Nos. 232880/1991, 364179/1992, EP-719782, etc., and methods based thereon. The other compounds are produced by the methods described in Japanese Patent Unexamined Publication No. 291983/1995, WO96/01267, EP-524023, etc., and methods based thereon.

Although the polyethylene glycol for the present invention appropriately has a weight-average molecular weight of about 200 to about 9,000, the weight-average molecular weight is not subject to limitation, as long as the object of the present invention is accomplished. For obtaining a liquid composition, a polyethylene glycol having a weight-average molecular weight of about 400 to about 600 is used. For obtaining a composition in a solid dispersion composition, a polyethylene glycol having a weight-average molecular weight of about 4,000 to about 6,000 is used. In the present specification, the term weight-average molecular weight is defined as a molecular weight based on pullulan as determined by gel permeation chromatography (GPC). Weight-average molecular weight was determined using the TSKgel GMPWxL GPC column (produced by Tosoh Corporation) and the L-3300 RI monitor (produced by Hitachi Ltd.), with distilled water as a mobile phase. Although these polyethylene glycols may be used alone, they may also be used as a mixture of 2 or more kinds.

The polyethylene glycol derivatives used in the present invention include, for example, fatty acid esters of polyethylene glycol and ether derivatives of polyethylene glycol, preferably polyglycolized glycerides, e.g., those represented by general formula (III):

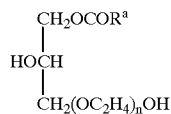

wherein $R^a$ is a $C_{8-12}$ alkyl group; n is an integer from 4 to 300. The carbon number of the fatty acid moiety of the polyglycolized glyceride is preferably of a moderate chain (8 to 12 carbon atoms). HLB is preferably as high as possible, specifically not less than 8. HLB can be adjusted by appropriately choosing the fatty acid in the polyglycolized glyceride and the carbon chain length of the polyethylene glycol.

Such polyglycolized glycerides include, for example, Labrasol (derived from coconut oil, fatty acid composition caprylic acid/capric acid, polyethylene glycol molecular weight 400, HLB 14), Labrafac CM-10 (derived from coconut oil, fatty acid composition caprylic acid/capric acid, polyethylene glycol molecular weight 400, HLB 10), Labrafil M10 (derived from corn oil, fatty acid composition linoleic acid, polyethylene glycol molecular weight 600, HLB 10), Labrafil NA10 (derived from apricot fruit, fatty acid composition oleic acid, polyethylene glycol molecular weight 600, HLB 10), all available from Gattefosse Company; Cremophor EL (fatty acid composition triricinoleic acid, HLB 13.5), available from BASF Company; Tagat TO (fatty acid composition trioleic acid, HLB 11.3), available from Goldschmidt Chem. Company. These may be used in a mixture of 2 or more kinds. When they are used in a mixture, the mixture's HLB is desirably not less than 8.

The ratio by weight of a polyethylene glycol and a derivative thereof to the non-peptide osteogenesis-promoting substance in the pharmaceutical composition of the present invention is about 0.5 to about 2,000 times, preferably about 2 to about 200 times, and more preferably about 5 to about 50 times.

The pharmaceutical composition of the present invention can preferably incorporate a glycerin fatty acid ester, in addition to the above-described polyethylene glycol or a derivative thereof. The glycerin fatty acid ester used in the present invention may be a mono-, di- or tri-glyceride with a fatty acid. The fatty acid is exemplified by $C_6$–$C_{22}$ aliphatic carboxylic acids such as caproic acid ($C_6$), caprylic acid ($C_8$), capric acid ($C_{10}$), lauric acid ($C_{12}$), myristic acid ($C_{14}$), palmitic acid ($C_{16}$), stearic acid ($C_{18}$), arachic acid ($C_{20}$) and behenic acid ($C_{22}$), with preference given to moderate-chain ($C_8$–$C_{12}$) fatty acids.

The ratio of esterified hydroxyl groups to all hydroxyl groups in said glycerin fatty acid ester (degree of esterification) is preferably not less than about 60%, more preferably not less than about 80%. Although glycerin fatty acid esters may be used singly or in combination of 2 or more kinds, they are preferably used as appropriate so that the degree of esterification is not less than about 60%, more preferably not less than about 80%.

The glycerin fatty acid ester is preferably a fatty acid triglyceride consisting of 1 glycerin molecule and 3 fatty acid molecules bound thereto via ester linkage (triacyl glycerin). These fatty acids involving ester linkage may be identical or different, with preference given to saturated fatty acids having 8 to 18 carbon atoms. Saturated fatty acids having 8 to 12 carbon atoms are particularly preferred.

Such glycerin fatty acid esters include, for example, MIGLYOL 810 (caprylic acid/capric acid triglyceride; fatty acid composition: 65–75% caprylic acid and 25–35% capric acid), MIGLYOL 812 (caprylic acid/capric acid triglyceride; fatty acid composition 50–65% caprylic acid and 30–45% capric acid), MIGLYOL 829 (succinic acid di(caprylic acid/capric acid)glycerile; fatty acid composition: 35–45% caprylic acid, 20–30% capric acid and 12–16% succinic acid), MIGLYOL 840 (dicaprylic acid propylene glycol; fatty acid composition: 65–80% caprylic acid and 15–30% capric acid), DYNASAN 110 (caprylic acid triglyceride), DYNASAN 112 (lauric acid triglyceride), DYNASAN 114 (myristic acid triglyceride), DYNASAN 116 (palmitic acid triglyceride), DYNASAN 118 (stearic acid triglyceride), commercially available from HÜLS AKTIENGESELLSCHAFT, Germany; and TRIESTER F-810 (caprylic acid/capric acid triglyceride), commercially available from Nikko Chemicals (Tokyo). These fatty acids may be used in a mixture of 2 or more kinds.

The glycerin fatty acid ester is used in a ratio by weight of about 0 to about 10 times, preferably about 0 to about 2 times, that of the above-described polyethylene glycol or a derivative thereof. Also, the glycerin fatty acid ester is used as appropriate so that its ratio by weight to the non-peptide osteogenesis-promoting substance is about 0.5 to about 2,000 times, preferably about 2 to about 200 times.

The organic solvent used to produce the pharmaceutical composition of the present invention preferably has a boiling point of not higher than 120° C. The organic solvent is exemplified by alcohols (e.g., methanol, ethanol), acetonitrile, aromatic hydrocarbons (e.g., benzene, toluene, xylene), halogenated hydrocarbons (e.g., dichloromethane, dichloroethane), and fatty acid esters (e.g., ethyl acetate, butyl acetate), ethanol, acetonitrile, etc. being commonly used. These solvents may be used in a mixture of 2 or more kinds at appropriate ratios. Also, to increase the active ingredient content in the pharmaceutical composition, the above-described organic solvent may be supplemented with propylene glycol or a fatty acid glyceride.

In preparing a pharmaceutical composition of the present invention, a non-peptide osteogenesis-promoting substance (active ingredient), polyethylene glycol or a derivative thereof, and, where necessary, a glyceride and the above-described organic solvent are mixed to yield a solution. While the order of mixing is not limited, normally, it is preferable that a polyethylene glycol or a derivative thereof and an organic solvent be added to the active ingredient. Although the concentration of the active ingredient in the organic solvent solution varies depending on the kinds of active ingredient and organic solvent, it is normally chosen over the range from about 0.1% to about 80% (w/w). Preferably, the concentration is about 0.5% to about 50% (w/w), more preferably about 1% to about 30% (w/w). If the active ingredient is difficult to dissolve, warming is preferred. In such case, warming temperature may be set at any level below 100° C.

The organic solvent is then removed from the thus-prepared solution by a known method. For example, the organic solvent is distilled off under reduced pressure. Alternatively, the organic solvent is removed, while nitrogen gas is parged under heating using a hot water bath etc. These methods may be used in combination to remove the organic solvent. For preparing the pharmaceutical composition of the present invention in a liquid form, the resulted liquid substance is filtered to yield the desired preparation. Alternatively, in consideration of the dosage form or stability, a liquid substance containing the active ingredient may be filled into soft capsules etc. For preparing the pharmaceutical composition of the present invention in a solid dispersion form, the residue on solvent distillation is rapidly cooled and vacuum dried to yield the desired preparation. The solid dispersion obtained may be subjected to size reduction using an appropriate filter.

The non-peptide osteogenesis-promoting substance content in the pharmaceutical composition obtained above is preferably about 0.05 to about 70% (w/w) relative to the pharmaceutical composition. More preferably, the content is about 2 to about 50%, contents of about 10 to about 30% being most preferably used.

The thus-obtained pharmaceutical composition of the present invention (1) permits solubilization of a water-insoluble or sparingly soluble active ingredient, (2) improves the absorbability of the active ingredient and markedly increases the bioavailability, and (3) improves the stability of the active ingredient in the preparation and in blood.

The pharmaceutical composition of the present invention may be administered usually orally in the form of a liquid preparation as it is, or may be filled in soft capsules or like to yield an oral preparation, when it is obtained in a liquid form. When the pharmaceutical composition of the present invention is in a solid dispersion, it can be packed in capsules, or shaped into pellets, fine granules, granules or tablets to yield an oral preparation. Moreover, such preparations may be shaped into suppositories such as rectal preparations, and non-oral preparations for topical administration (e.g., intramuscular, subcutaneous, intra-articular injections, embedding preparations, soft ointments etc.).

Although the pharmaceutical composition of the present invention may be used as such, it may also be prepared as various dosage forms according to the methods of administration. When the composition is a solid dispersion, for example, it may be shaped into solid forms such as spheres, rods, needles, pellets and films, in the presence of additional additives added as necessary. Also, by preparing the composition as an aqueous suspension together with appropriate dispersing agents (e.g., surfactants such as Tween 80 and HCO-60, carboxymethyl cellulose, sodium alginate, hyaluronic acid, polysorbate), preservatives (e.g., methyl paraben, propyl paraben), isotonizing agents (e.g., sodium chloride, mannitol, sorbitol, glucose), buffers (e.g., calcium carbonate), pH adjusting agent (e.g., sodium phosphate, potassium phosphate), etc., to yield a preparation for injection. Also, the pharmaceutical composition of the present invention may be prepared as an injectable preparation as an oily suspension by dispersing it together with a vegetable oil such as sesame oil or corn oil with or without a phospholipid such as lecithin. For obtaining these preparations, the methods such as described in the Pharmacopoeia of Japan, 12th edition are used.

Because the pharmaceutical composition of the present invention and the preparation based thereon possesses an excellent osteogenesis-promoting activity and shows very high bioavailability and stability even in oral administration to the body, it can be used to prevent and treat bone diseases (e.g., bone fractures, re-fractures, osteoporosis, osteomalacia, Paget's disease of bone, sclerotic spondylitis, osteoarthritis rheumatoid arthritis, knee arthritis deformans, joint tissue destruction in similar diseases), to repair bone tissue after surgery for multiple myeloma, lung cancer, breast cancer, etc., to regenerate periodontal tissue in periodontal diseases, and for other purposes. Because the pharmaceutical composition of the present invention shows high bioavailability in administration to osteoporosis patients, in particular, it is useful as a prophylactic/therapeutic drug for the disease. Specifically, the compound of the formula (I) (hereinafter referred to briefly as compound (I)) or a salt thereof, for example, is known to possess potent bone resorption suppressing activity, bone metabolism-improving activity and osteogenesis-promoting activity (Japanese Patent Unexamined Publication No. 364179/1992 etc.); by applying the present invention, an excellent preventing (prophylactic)/treating (therapeutic) drug for bone diseases (e.g., osteoporosis) can be obtained.

The pharmaceutical composition of the present invention and a preparation based thereon can also be used concomitantly with other agents for treating bone diseases. When the osteogenesis-promoting substance used is compound (I) above or a salt thereof, for example, examples of drugs concomitantly used include, for example, calcium preparations (e.g., calcium carbonate), calcitonin preparations, vitamin D preparations (e.g., alpha calcidol), sex hormones (e.g., estrogen, estradiol), prostaglandin A1, bisphosphonic acids, ipriflavones, fluorine compounds (e.g., sodium fluoride), vitamin $K_2$, bone morphogenic protein (BMP), fibroblast growth factor (FGF), platelet-derived growth factor (PDGF), transforming growth factor (TGF-$\beta$), insulin-like growth factors 1 and 2 (IGF-1, -2) and parathyroid hormone (PTH).

Because the pharmaceutical composition of the present invention and its preparations are low in toxicity, they can be safely used in mammals (e.g., humans, bovines, horses, pigs, dogs, cats, mice, rats, rabbits).

Although the dose of the pharmaceutical composition of the present invention and its preparations varies depend on the kind and content of the non-peptide osteogenesis-promoting substance, the kind of polyethylene glycol used, dosage form, subject animal species, etc., it may be set at any level, as long as it provides an effective amount of said non-peptide osteogenesis-promoting substance. When a soft capsule solution of the present invention containing compound (I) above or a salt thereof, for example, is used, it may be orally administered to an adult osteoporosis patient (about 60 kg) at about 0.1 mg to about 500 mg, preferably about 10 mg to about 200 mg, daily in 1 to 3 divided doses, based on the active ingredient.

BEST MODE FOR CARRYING OUT THE INVENTION

The present invention is hereinafter described in more detail by means of the following Comparative Examples, Working Examples and Test Examples, which are not to be construed as limitative. "Room temperature" as used herein means about 0° C. to about 30° C.

EXAMPLES

Comparative Example 1

To 150 mg of (2R,4S)-(−)-N-[4-(diethoxyphosphorylmethyl)phenyl]-1,2,4,5-tetrahydro-4-methyl-7,8-methylendioxy-5-oxo-3-benzotiepine-2-carboxamide (compound A) 0.5% methylcellose aqueous solution was added to whole volume at 7.5 ml, then dispersed by bath type ultrasonic homogenizer to yield uniform suspension.

Example 1

To 32.5 mg of (2R,4S)-(−)-N-[4-(diethoxyphosphorylmethyl)phenyl]-1,2,4,5-tetrahydro-4-methyl-7,8-methylendioxy-5-oxo-3-benzotiepine-2-carboxamide (hereinafter referred as compound A), 6.5 ml 1:9 (v/v) mixture of dimethylsulfoxide and polyethylene glycol 400 was added and dissolved by stirring to provide a transparent solution.

Example 2

To 150 mg of compound A 2.25 ml polyethylene glycol 400 (produced by Höechst Inc., polyethylen glycol Hoechst 400/DAB8), 2.25 ml ethanol and 3.0 ml propylene glycol (produced by Wako Pure Chemical Co.) was added, then compound A was dissolved by occasional stirring under 70° C. hot water bath warming. After the compound A was completely dissolved, ethanol was removed from the solution by blowing nitrogen gas under the 60° C. hot water bath heating. The resulting solution was filtrated to provide a transparent solution. The concentration of compound A in the resulting solution was 29 mg/ml.

Example 3

To 750 mg of compound A, 6.75 g of polyethylene glycol 6000 (produced by Wako Pure Chemical Co.) and 20 ml acetonitrile was added and occasionally stirred under 70° C. hot water bath heating until compound A was completely dissolved. Then the solution was subjected to the rotating evaporator to remove acetonitrile gradually. After acetonitrile was removed, the residue was crystallized by rapid ice-cooling and −20° C. for 1 hr, and dried under reduced pressure at 40° C. for 24 hours. The resulting powder was pulverized in mortar and sieved with 42-mesh and 60-mesh sieve to yield microgranules glassified by size to 250 μm to 350 μm.

Example 4

To 100 mg of compound A, 4 ml polyglycolized polyglyceride (tradename: Labrasol, produced by Gattefosse) 1 ml trigricericle (tradename: Miglyol 812, produced by Hüls Akitiengesellshaft) and 5 ml methanol, and the mixture was stirred for dissolving at room temperature. The resulting solution was subjected to rotating evaporation to remove methanol gradually. The resulting solution was stored in well-closed container in which the atmosphere had been replaced with nitrogen gas.

Experimental Example 1

The solution (0.1 ml) cprepared in Example 1 was intravenously administered to male 11-week-old SD rats (Body weight about 500 mg Clea Japan) from caudal vein (1 mg/kg, n=3). Blood was collected from caudal vein periodicaly and subjected to 12,000 rpm centrifugation for 10 minutes to determine the plasma concentration of compound A. The result is shown in Table 1. The area under the plasma level of drug time curve (AUC) calculated by trapezoidal rule was 1.511 μg.hr/ml.

TABLE 1

| Time | plasma concentration (μg/ml) |
|---|---|
| 5 min | 3.461 ± 0.294 |
| 10 min | 2.406 ± 0.158 |
| 15 min | 1.644 ± 0.092 |
| 30 min | 0.778 ± 0.113 |
| 1 hr | 0.225 ± 0.127 |
| 2 hr | 0.122 ± 0.083 |
| 4 hr | 0.035 ± 0.035 |
| 8 hr | 0 |
| 24 hr | 0 |

Experimental Example 2

The suspension prepared in Comparative Example 1 and the solution prepared in Example 2 was orally administered to male 7-week-old SD rats (Body weight about 260 g, Clea Japan) (50 mg/kg, n=5). Blood was collected periodicaly from the caudal vein and subjected to 12,000 rpm centrifugation for 10 minutes to determine the plasma concentratin of compound A. The results are shown in Table 2. The AUC of the suspension and the solution calculated by trapezoidal rule were respectively 7.590 μg.hr/ml and 33.608 μg.hr/ml. The absolute bioavailability determined by using the AUC valve obtained in Example 1 was based on the postulate that there is a linear correlation between the dosage and the blood level of drug was respectively 10.1% and 44.5%.

TABLE 2

| Time | plasma level after administration of the suspention (μg/ml) | plasma level after administration of the solution (μg/ml) |
|---|---|---|
| 30 min | 0.324 ± 0.048 | 3.390 ± 0.763 |
| 1 hr | 0.203 ± 0.037 | 1.194 ± 0.350 |
| 2 hr | 0.496 ± 0.038 | 5.075 ± 1.002 |
| 4 hr | 0.577 ± 0.099 | 4.815 ± 0.813 |
| 6 hr | 0.461 ± 0.078 | 2.260 ± 0.255 |
| 8 hr | 0.346 ± 0.039 | 0.953 ± 0.163 |
| 24 hr | 0.177 ± 0.057 | 0.191 ± 0.039 |

It is recognized from the results shown in Table 2, in which the oral absorption of the compound A-polyethylene glycol 400 solution of the present invention was 4 fold or more than that of the compound A-methylcellose suspension, that a marked increase in oral absorption of compound A was caused by addition of polyethylene glycol.

Experimental Example 3

Aqueous suspension of the compound A-polyethylene glycol 6000 solid dispersion prepared in Example 3 was orally administered to mole 7-week-old SD rats (Body weight about 265 g, Clea Japan) (10 mg/kg, n=4). Blood was collected from cauadal vein periodicaly and subjected to 12,000 rpm centrifugation for 10 minutes to determine the plasma concentration of compound A. The result is shown in Table 3. The AUC calculated by trapezoidal rule was 2.628 μg.hr/ml. The absolute bioavailability determined by using the AUC value obtained in Experimental Example 1 based on a postulate that there is a linear correlation between the dose and the blood level of a drug was 17.4%.

TABLE 3

| Time | plasma level (μg/ml) |
|---|---|
| 30 min | 0.150 ± 0.042 |
| 1 hr | 0.178 ± 0.042 |
| 2 hr | 0.295 ± 0.024 |
| 4 hr | 0.165 ± 0.021 |
| 6 hr | 0.169 ± 0.072 |
| 8 hr | 0.150 ± 0.079 |
| 24 hr | 0 |

It is recognized from the results in Table 3, in which the compound A-polyethylene glycol 6000 solid dispersion of the present invention showed about 1.7 fold of oral absorption than that of the compound A-methylcellose suspension, that a marked increase in oral absorption of of compound A was caused by the addition of the polyethylene glycol.

Experimental Example 4

The compound A-Labrasol-Miglyol 812 solution prepared in Example 4 was orally administered to male 7-week-old SD rats (body weight about 250 g, Clea Japan) (10 mg/kg, n=4). Blood was collected from the caudal vein periodicaly and subjected to 12,000 rpm centrifugation for 10 minutes to determine the plasma level of compound A. AUC calculated by trapezoidal rule was 8.001 μg.hr/ml. The absolute bioavailability determined by using the AUC value obtained in Example 1 based on a postulate that there is a linear correlation between the dose and the blood level of a drug was 59%.

TABLE 4

| Time | plasma level (μg/ml) |
|---|---|
| 15 min | 1.265 ± 0.268 |
| 30 min | 2.188 ± 0.143 |
| 1 hr | 2.225 ± 0.507 |
| 2 hr | 2.160 ± 0.183 |
| 4 hr. | 0.449 ± 0.052 |
| 6 hr | 0.218 ± 0.022 |
| 8 hr | 0.103 ± 0.024 |
| 24 hr | 0.001 ± 0.001 |

It is recognized from the results in Table 4, in which the compound A-Labrasol-Miglyol 812 solution of the present invention showed about 5-fold of the oral absorption than that of the compound A-methylcellose suspension, that a marked increase of the oral absorption of compound A was caused by the addition of polyglycolized glyceride and glyceline fatty acid ester.

INDUSTRIAL APPLICABILITY

The pharmaceutical composition of the present invention can be used as a superior medicament for preventing and/or treating bone diseases in the clinical field, since it can be administered to the patient in need safely and easily and provides extremely high bioavailability compared with that of medicaments known hereto.

What is claimed is:

1. A pharmaceutical composition for oral administration which comprises a non-peptide osteogenesis-promoting substance and a polyethylene glycol or a derivative thereof, wherein the weight ratio of the polyethylene glycol or a derivative thereof relative to the non-peptide osteogenesis-promoting substance is from about 0.5 to about 2,000 times.

2. The pharmaceutical composition according to claim 1, wherein the non-peptide osteogenesis-promoting substance is a compound represented by the formula or salt thereof:

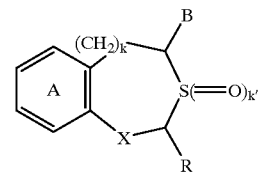

wherein ring A is an optionally substituted benzene ring; R is a hydrogen atom or an optionally substituted hydrocarbon group; B is an optionally esterified or amidated carboxyl group; X is —CH(OH)— or —CO—; k is 0 or 1; and k' is 0, 1 or 2.

3. The pharmaceutical composition according to claim 2, wherein the ring A is a benzene ring which may be substituted by 1 or 2 substituents selected from the group consisting of halogen atoms, $C_{1-10}$ alkyl groups, $C_{1-10}$ alkoxy groups, alkylendioxy groups represented by the formula: —O—$(CH_2)_n$—O—, wherein n is an integer from 1 to 3 and $C_{1-10}$ alkylthio groups.

4. The pharmaceutical composition according to claim 2, wherein B is an optionally substituted carbamoyl group of the formula: —CON($R_1$)($R_2$), wherein $R_1$ and $R_2$ are independently a hydrogen atom, an optionally substituted hydrocarbon group or an optionally substituted 5 to 7 membered heterocyclic group.

5. The pharmaceutical composition according to claim 4, wherein $R_1$ is a hydrogen atom or a $C_{1-10}$ alkyl group, and $R_2$ is (i) a phenyl or phenyl-$C_{1-3}$ alkyl group which may be substituted by a halogen atom, a $C_{1-6}$ alkoxy group, a mono- or di-$C_{1-6}$ alkoxyphosphoryl group, a mono- or di-$C_{1-6}$ alkoxyphosphoryl-$C_{1-3}$ alkyl group, a moiety of the formula:

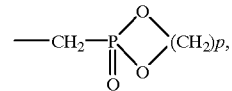

wherein p is an integer of 2 to 4, or a $C_{1-6}$ alkoxy-carbonyl group or (ii) a 5- or 6-membered heterocyclic group containing 1 or 2 nitrogen atom(s) or 1 nitrogen atom and 1 sulfur atom, which may be substituted by a phenyl group.

6. The pharmaceutical composition according to claim 2, wherein R is a hydrogen atom, a $C_{1-6}$ alkyl group or a phenyl group.

7. The pharmaceutical composition according to claim 2, wherein k is 1 and k' is 0.

8. The pharmaceutical composition according to claim 1, wherein the non-peptide osteogenesis-promoting substance is an optically active compound represented by the formula:

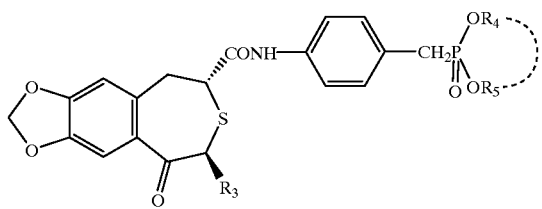

wherein R₃ is a lower alkyl group; and R₄ and R₅ are independently a lower alkyl group or bind together to form a lower alkylene group.

9. The pharmaceutical composition according to claim 8, wherein R$_3$, R$_4$ and R$_5$ are independently a C$_{1-6}$ alkyl group.

10. The pharmaceutical composition according to claim 1, wherein the non-peptide osteogenesis-promoting substance is (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide.

11. The pharmaceutical composition according to claim 8, which comprises (2R,4S)-(−)-N-[4-(diethoxyphosphorylmethyl)phenyl]-1,2,4,5-tetrahydro-4-methyl-7,8-methylenedioxy-5-oxo-3-benzothiepine-2-carboxamide and a polyethylene glycol.

12. The pharmaceutical composition according to claim 11, wherein the weight ratio of (2R,4S)-(−)-N-[4-diethoxyphosphorylmethyl)phenyl]-1,2,4,5-tetrahydro-4-methyl-7,8-methylenedioxy-5-oxo-3-benzothiepine-2-carboxamide relative to the pharmaceutical composition is about 0.05 to about 70% (w/w).

13. The pharmaceutical composition according to claim 1, wherein the weight-average molecular weight of the polyethylene glycol is about 200 to about 9,000.

14. The pharmaceutical composition according to claim 1, wherein the derivative of polyethylene glycol is a polyglycolized glyceride.

15. The pharmaceutical composition according to claim 14, wherein the HLB of the polyglycolized glyceride is not less than 8.

16. The pharmaceutical composition according to claim 1, which further comprises a glycerin fatty acid ester.

17. The pharmaceutical composition according to claim 16, wherein the glycerin fatty acid ester is a fatty acid triglyceride.

18. A pharmaceutical composition for oral administration which is produced by removing the organic solvent from a solution comprising a non-peptide osteogenesis-promoting substance and a polyethylene glycol or a derivative thereof in an organic solvent, wherein the weight ratio of the polyethylene glycol or a derivative thereof relative to the non-peptide osteogenesis-promoting substance is from about 0.5 to about 2,000 times.

19. A method for producing the pharmaceutical composition of claim 1, which comprises dissolving a non-peptide osteogenesis-promoting substance and a polyethylene glycol or a derivative thereof in an organic solvent, and removing the solvent, wherein the weight ratio of the polyethylene glycol or a derivative thereof relative to the non-peptide osteogenesis-promoting substance is from about 0.5 to about 2,000 times.

20. The method according to claim 9, wherein the organic solvent comprises 1 to 3 solvent(s) selected from the group consisting of alcohols, acetonitrile, aromatic hydrocarbons, halogenated hydrocarbons and fatty acid esters.

21. The method according to claim 20, wherein the solvent further comprises propylene glycol.

22. The method according to claim 19, wherein the solvent is methanol, ethanol or acetonitrile.

23. The method according to claim 19, wherein the concentration of the non-peptide osteogenesis-promoting substance in the organic solvent solution is from about 0.01% (w/w) to about 80% (w/w).

24. A method for improving bioavailability of a pharmaceutical composition for oral administration comprising a non-peptide osteogenesis-promoting substance, which comprises adding a polyethylene glycol or a derivative thereof to the pharmaceutical composition.

25. A method for treating or preventing a bone disease in mammals, comprising orally administering to a subject in need thereof an effective amount of a pharmaceutical composition according to claim 1.

26. The method according to claim 25, wherein the bone disease is osteoporosis.

27. The pharmaceutical composition according to claim 1, wherein the non-peptide osteogenesis-promoting substance is a nonsteroidal compound.

28. The pharmaceutical composition according to claim 1, wherein the non-peptide osteogenesis-promoting substance is selected from a group consisting of sulfur-containing heterocyclic compounds; benzopyrane derivatives; phosphonic acid derivatives; prostaglandin A$_1$ derivatives; vitamin D$_3$ derivatives; benzylphosponic acid derivatives; bisphosphonic acids; vitamin K$_2$ derivatives; the compounds of claim 5; and a salt thereof.

29. The pharmaceutical composition according to claim 1, wherein the non-peptide osteogenesis-promoting substance is selected from a group consisting of N-(4-diethoxyphosphorylmethylphenyl)-4-oxo-4H-1-benzopyrane-2-carboxamide; diethyl 4-(7-cyclohexyl-3,4-dihydro-2-naphthalenecarboxamide) benzylphosphonate; the compounds of claim 5; and a salt thereof.

30. The pharmaceutical composition according to claim 1, wherein the non-peptide osteogenesis-promoting substance is a compound of claim 5 or a salt thereof.

* * * * *